(12) United States Patent
Bodenbach et al.

(10) Patent No.: US 8,354,235 B2
(45) Date of Patent: Jan. 15, 2013

(54) METHOD FOR INCREASING THE DYNAMIC MEASURING RANGE OF TEST ELEMENTS BASED ON SPECIFIC BINDING REACTIONS

(75) Inventors: Ludger Bodenbach, Heiligkreuzsteinach (DE); Juergen Schaeffler, Weinheim (DE); Juergen Spinke, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/557,279

(22) Filed: Nov. 7, 2006

(65) Prior Publication Data

US 2007/0259450 A1    Nov. 8, 2007

Related U.S. Application Data

(63) Continuation of application No. PCT/EP2005/005016, filed on May 10, 2005.

(30) Foreign Application Priority Data

May 12, 2004  (DE) .......................... 10 2004 023 402

(51) Int. Cl.
*G01N 33/533* (2006.01)

(52) U.S. Cl. ...... 435/7.1; 435/7.92; 435/7.93; 435/7.94; 435/810; 435/969; 435/970; 435/973; 435/975; 436/518; 436/531; 436/533; 436/534; 436/805; 436/514

(58) Field of Classification Search .................... 435/7.1, 435/7.92, 7.93, 7.94, 810, 969, 970, 973, 435/975; 436/514, 518, 531, 533, 534, 805
See application file for complete search history.

(56) References Cited

U.S. PATENT DOCUMENTS

| 4,595,661 A | 6/1986 | Cragle et al. |
| 4,743,542 A | 5/1988 | Graham, Jr. et al. |
| 4,861,711 A | 8/1989 | Friesen et al. |

(Continued)

FOREIGN PATENT DOCUMENTS

| EP | 0291194 B1 | 11/1988 |

(Continued)

OTHER PUBLICATIONS

Hampl, J., Hall, M., Mufti, N., Yao, Y., MacQueen, D., Wright, W., Cooper, D. "Upconverting Phosphor Reporters in Immunochromatographic Assays", Analytical Biochemistry 288, 176-187 (2001).

(Continued)

*Primary Examiner* — Chris L Chin
(74) *Attorney, Agent, or Firm* — McDonnell Boehnen Hulbert & Berghoff LLP (57) ABSTRACT

The invention concerns a method for increasing the dynamic measuring range of especially immunological test elements in particular immunological chromatography test strips that can be evaluated optically that are based on specific binding reactions. The invention enables the dynamic measuring range of test elements based on specific binding reagents, especially of immunological test elements to be shifted towards higher analyte concentrations without impairing the lower detection limit. For this purpose it is proposed according to the invention that at least two zones are provided in or on the test element which contain reagents that generate detectable signals of different strengths due to different affinities for the analyte (for example in the case of antibodies that have different affinities for the analyte) or due to different principles of interaction with the analyte or with other reagents involved in the analyte detection (for example antibodies directed against the analyte in one zone and an analyte analogue in another zone). The signals in the at least two zones are used to evaluate the analyte concentration-signal strength relationship and are used to determine the analyte by means of a suitable method (correlation).

15 Claims, 5 Drawing Sheets

U.S. PATENT DOCUMENTS

| | | | |
|---|---|---|---|
| 4,916,056 A * | 4/1990 | Brown et al. | 435/7.92 |
| 5,073,484 A | 12/1991 | Swanson et al. | |
| 5,141,850 A | 8/1992 | Cole et al. | |
| 5,458,852 A | 10/1995 | Buechler | |
| 5,569,608 A * | 10/1996 | Sommer | 436/518 |
| 5,585,241 A | 12/1996 | Lindmo | |
| 5,591,645 A | 1/1997 | Rosenstein | |
| 5,717,778 A | 2/1998 | Chu et al. | |
| 5,856,203 A * | 1/1999 | Robinson et al. | 436/518 |
| 6,248,597 B1 | 6/2001 | Eda et al. | |
| 6,506,612 B2 | 1/2003 | Kang et al. | |
| 6,924,153 B1 * | 8/2005 | Boehringer et al. | 436/514 |
| 6,998,246 B2 * | 2/2006 | Schaffler et al. | 435/7.9 |
| 7,790,439 B2 * | 9/2010 | Nadaoka et al. | 435/287.2 |
| 2002/0055126 A1 | 5/2002 | Schaffler et al. | |
| 2003/0068665 A1 | 4/2003 | Kawamura et al. | |
| 2003/0119204 A1 | 6/2003 | Wei et al. | |
| 2005/0112780 A1 * | 5/2005 | Song | 436/514 |

FOREIGN PATENT DOCUMENTS

| | | |
|---|---|---|
| EP | 1293780 * | 3/2003 |
| EP | 1361435 A1 | 11/2003 |
| WO | WO 97/06439 | 2/1997 |
| WO | WO 00/31538 | 6/2000 |
| WO | WO 03014740 A1 * | 2/2003 |

OTHER PUBLICATIONS

"Assay Formats", disclosure by OraSure Technologies Inc., Bethlehem, PA, USA, on www.orasure.com, (May 23, 2003).

Niedbala, R. Sam, et al., "Detection of Analytes by Immunoassay Using Up-Converting Phosphor Technology", Analytical Biochemistry, 293, pp. 22-30, 2001.

Notice of Reasons for Rejection, JP2007-512059, prepared by Hiraki & Associates, Mailing Date: Oct. 20, 2009 (2 pages).

* cited by examiner

METHOD FOR INCREASING THE DYNAMIC MEASURING RANGE OF TEST ELEMENTS BASED ON SPECIFIC BINDING REACTIONS

BACKGROUND OF THE INVENTION

The present invention relates generally to analytical test devices and, more particularly, to a method for increasing the dynamic measuring range of test elements based on specific binding reactions.

Immunological test strips are a widespread device for the rapid determination of drugs, pregnancy hormones, infectious diseases or so-called "cardiac markers" such as troponin T. In this connection qualitative tests that are read by purely visual means and often only yield a "yes-no" answer as well as quantitative tests which are evaluated by means of a reading instrument are widely used.

Rapid tests for immunologically detectable substances are known for numerous different parameters, for example from WO 97/06439, EP 0 291 194, U.S. Pat. Nos. 5,591,645, 4,861,711, 5,141,850, 6,506,612, 5,458,852, 5,073,484. In this case the immunological detection reagents (essentially labelled and unlabelled antibodies or antigens) are provided in a dry form on a support which allows the transport of a sample liquid (in particular body fluids such as blood, serum, plasma, urine, saliva, etc.) on or in the support. For this purpose the support is preferably capillary-active and is for example a membrane or a plastic support provided with capillary channels (such as, e.g., in U.S. Pat. No. 5,458,852). Among those skilled in the relevant art these are often referred to as immunological or immunochromatographic test strips or test devices. These terms as well as the term "carrier-bound immunological tests" or "carrier-bound immunological test elements" are often used synonymously and should also be interchangeable in the following.

In the case of simple systems and in particular in the case of purely qualitative analyses (where only the information "the analyte is present or not present" is of interest) such immunological test devices are often evaluated by purely visual means. This principle is now widely accepted in the market especially in the field of pregnancy tests.

(Semi)quantitative immunological rapid tests are usually evaluated with the aid of corresponding measuring instruments that are matched to the respective test strip. Different measuring principles are used depending on the type of labelling of the reagents of the test device used to detect the analyte. Optical detection methods and especially the measurement of reflectance and fluorescence are commonly used and simple to handle.

Many systems from the prior art ensure that the analyte detection zone (also abbreviated to "detection zone" in the following) and control zone are spatially narrowly delimited and arranged clearly separated from one another on the test device. For this purpose it has proven to be particularly advantageous to apply appropriate binding reagents in the form of lines or broken lines on the test device. Hence in order to evaluate the test device, spatially resolving optical systems such as for example camera chips or 2-dimensional or 3-dimensional photodiode arrays are often present in the measuring instrument for the purpose of evaluating the analyte detection zones and control zones. The signals of the optical systems are then converted by an appropriate evaluation software into concentration values and displayed.

With the immunological test devices of the prior art it is not possible to quantitatively detect any concentrations of the analyte in the sample. Towards the lower end, i.e., with regard to the lower detection limit, the measuring range is for example limited by the affinity and selectivity of the binding partners (usually antibodies) that are used and by the sensitivity of the detection optics which is limited with regard to the labels that are used. Saturation effects limit the measuring range towards the upper end, i.e., with regard to the dynamic measuring range. Thus in the case of analytes which can occur in very high concentrations in the sample, it is often not possible to provide an adequate amount of binding partner in the test device. In particular, in the analyte detection zones and control zones where the binding partners are arranged in a very restricted space on the test device, it is not possible to accommodate as much binding partner as would be desired. This can be particularly problematic in those cases in which a low detection limit for the analyte is required (and one therefore endeavors to concentrate the binding partners in the detection zone as strongly as possible, i.e., to accommodate them in a restricted space and thus due to the limited availability of binding sites on the test device only a relatively small amount of binding partner can be provided) but the analyte can be present in the sample in very variable amounts, i.e., very low as well as very high analyte concentrations can occur. At high analyte concentrations the detection zone is saturated with corresponding detection reagents resulting in a saturation behavior of the analyte concentration-detection signal relationship: The detection signal no longer increases above a certain analyte concentration, the evaluation curve levels off and can no longer be appropriately evaluated.

This is aggravated by the fact that especially with sandwich immunoassays not only is a levelling off of the curve to be observed at very high analyte concentrations which reflects the relationship between the analyte concentration and detection signal but also even a decrease of the signal with increasing analyte concentrations. This is referred to as the "high dose Hook effect": At very high analyte concentrations it is observed that the signal intensity of sandwich immunoassays which initially increases as the analyte concentration increases, decreases again. This is explained by the fact that the amount of antibody offered in the test is no longer sufficient to form a sandwich complex (i.e., a complex comprising two antibodies per antigen) with the analyte molecules (antigens) in every case. There is an increasing formation of complexes consisting of analyte and in each case one antibody which, however, on their own are no longer detected. Thus measuring results that are false-negative or too low may occur which of course should be avoided.

Especially the quantitative immunological test strips in which a signal is determined by reflectance measurements, still have in some cases considerable weaknesses compared to conventional analytical systems that are usually used in large laboratories. In particular, the precision and the dynamic measuring range is usually worse in the case of test strips. This limits in particular the field of application of the highly sensitive sandwich assays for example for therapeutic monitoring where the largest possible measuring range is desired.

Moreover, for some parameters such as myoglobin or D-dimer a low detection limit is required, on the one hand, but on the other hand, very high concentrations of these analytes can occur in the sample material which are sometimes considerably above the decision limit "normal-pathological". In these cases it would be desirable to have available test devices which have the largest possible measuring range in order to obtain reliable measured values without sample dilution. This would be of particular advantage for the use of such test devices to monitor the course of corresponding diseases.

In the prior art there has been no lack of concepts to solve the problems described above. However, up to now none of the proposals has been convincing in all points. In particular, the implementation of the concepts in the field of immunochromatographic test devices has not satisfactorily succeeded up to now.

U.S. Pat. No. 6,248,597 describes a heterogeneous agglutination immunoassay based on light scattering in which the dynamic measuring range is extended by mixing particles having different scattering properties. Binding partners having a high affinity for the analyte are immobilized on the particles which cause a large light scattering. In contrast, binding partners having a low affinity for the analyte are immobilized on the particles which cause a low light scattering.

A similar method is known from U.S. Pat. No. 5,585,241. In order to increase the dynamic measuring range, it proposes in connection with a flow cytometry immunoassay that two particles of different sizes are loaded with two antibodies having different affinities for the same antigen (small particles loaded with high-affinity antibody, large particles loaded with low-affinity antibody) and that an additional detectably-labelled antibody is used to detect the antigen by formation of a sandwich complex. The proposed system uses two different standard curves (one for each sort of particle) and allows a quantitative analyte determination by means of an ingenious software.

In order to avoid the Hook effect at high analyte concentrations (high dose Hook effect) U.S. Pat. No. 4,743,542 discloses a method in which, in addition to a detectably labelled antibody against the target antigen, a certain amount of the same but unlabelled antibody is simply added to the sample. As a result both antibodies compete for the analyte molecule and the oversaturation typical for the Hook effect only occurs, if at all, at higher antigen concentrations. As a result the dynamic measuring range is extended towards higher concentrations but at the expense of sensitivity. The use of low-affinity antibodies is proposed which have the same effect.

U.S. Pat. No. 4,595,661 describes heterogeneous sandwich immunoassays in which the Hook effect is avoided by using two soluble antibodies which have different affinities and specificities for the antigen, in addition to an immobilized capture antibody. The antibody having lower affinity only contributes significantly to the measuring signal at high antigen concentrations and hence prevents the Hook effect from becoming noticeable.

It is known from U.S. Pat. No. 5,073,484 that an immunologically detectable analyte can be quantitatively detected using several discrete, successive binding zones in a flow-through support. The number of zones in which the specific binding and detection reactions take place increases with an increasing amount of analyte in the sample. The number of zones which are colored after sample contact correlates with the amount of analyte in the sample. U.S. Pat. No. 5,073,484 proposes that the number of binding zones be increased in order to increase the accuracy and to extend the measuring range. A disadvantage of this is that an automatic evaluation of the binding zones requires a relatively complicated optical system which is able under certain circumstances to simultaneously detect and evaluate a large number of zones in order to thus allow a quantitative analyte determination. Moreover, the test devices have to be relatively long due to the relatively large number of discrete binding zones that are spatially separated from one another. Thus in order to ensure that the sample reliably migrates through the test device, it is necessary to use relatively large sample volumes which especially if it is intended to use whole blood samples, is also disadvantageous especially for reasons of sample collection.

WO 00/31538 describes immunochromatographic test strips in which one or more control zones are accommodated on an absorbent matrix in addition to an analyte detection zone. Binding partners for the analyte provided with a detectable label are bound to the matrix in the analyte detection zone as well as in the control zones. In this process exactly defined amounts of labelled binding partner are bound in the control zones where these amounts are independent of the amount of analyte in the sample. Different amounts of labelled binding partner are preferably bound in the control zones such that quasi internal comparative scales are present on the test strip. The control zones are used for calibration when evaluating the analyte detection zone. In order to increase the dynamic measuring range especially for non-linear concentration-measuring signal relationships, WO 00/31538 proposes that additional control zones are provided on the test strip.

In the case of immunochromatographic test strips which use fluorescent labels for analyte detection, it is known from J. Hampl et al., "Upconverting Phosphor Reporters in Immunochromatographic Assays", Analytical Biochemistry 288, 176-187 (2001) that the control zone (control line) which contains a species-specific antibody in an immobilized form can also be used to evaluate the measured signal in addition to the actual detection zone (target line) which contains an analyte-specific antibody in an immobilized form. A similar use is described by OraSure Technologies Inc., Bethlehem, Pa., USA, on www.orasure.com. The evaluation of the target line as well as control line is primarily used to eliminate variations in the measured signal that are due to the actual amount of liquid in the optically measured region of the test strip. As a result the sensitivity of the detection method (assay) is also indirectly increased (the dynamic measuring range is thus extended towards lower concentrations). In contrast an extension of the dynamic measuring range towards higher concentrations is not reported.

The dynamic measuring range of immunochromatographic test devices can also be de facto extended by diluting the sample material accordingly before analysis. An extension of the measuring range achieved in this manner is unsatisfactory since it requires additional handling steps that could potentially lead to errors in the analysis. Furthermore, especially in cases in which an analyte could occur in very high as well as in very low concentrations in similar samples, a controlled sample dilution is only advisable when the analyte is present in the sample at high concentrations but not in the reverse case since otherwise the concentration may fall below the lower detection limit as a result of the dilution and the analyte may be falsely not detected in the sample.

There has been previously a lack of simple and reliable methods for extending the dynamic measuring range of immunochromatographic test devices towards higher analyte concentrations without adversely affecting the lower detection limit for the analyte detection.

SUMMARY OF THE INVENTION

It is against the above background that the present invention provides certain unobvious advantages and advancements over the prior art. In particular, the inventors have recognized a need to extend the dynamic measuring range of test elements based on specific binding reactions and especially of immunological test elements towards higher analyte concentrations where in particular this should be made possible without impairing the lower detection limit.

In accordance with one embodiment of the present invention, a method for determining the concentration of an analyte in a sample is provided comprising a) providing a test element comprising at least one first zone and at least one second zone; b) contacting the sample with the test element and at least one reagent capable of specific binding reaction with the analyte; b) measuring a first detectable signal in the first zone of the test element, wherein the first signal results from the interaction of analyte if present in the sample with the reagent, and is dependent on the amount of the analyte in the sample; c) measuring a second detectable signal in the second zone of the test element, wherein the second signal results from the interaction of a portion of the reagent which has not interacted with the analyte or with the reagents in the first zone, and the second signal is also dependent on the amount of analyte in the sample; e) relating the first and the second signals to one another; and f) comparing the relation of the first and the second signals with a calibration curve.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

The numerals in the figures denote:
1 sample application zone
2 erythrocyte separation zone
3 detection zone
4 suction zone
5 support material
6 sample application matrix ("biotin fleece" and "gold fleece")
7 erythrocyte separation matrix
8 detection matrix
9 1st linear immobilization zone (detection line; analyte detection zone)
10 2nd linear immobilization zone (control line; control zone)
11 suction matrix Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

Although the present invention is not limited to specific advantages or functionality, it is noted that the present invention enables the dynamic measuring range of test elements based on specific binding reagents, especially of immunological test elements, to be shifted towards higher analyte concentrations without impairing the lower detection limit. For this purpose it is proposed according to the present invention that at least two zones are provided in or on the test element which contain reagents that generate detectable signals of different strengths due to different affinities for the analyte (for example in the case of antibodies that have different affinities for the analyte) or due to different principles of interaction with the analyte or with other reagents involved in the analyte detection (for example antibodies directed against the analyte in one zone and an analyte or analyte analogue in another zone). In this connection "different principles of interaction" can for example be different test principles such as sandwich complex formation in one zone and a competitive test procedure in the other zone. The signals in the at least two zones are used to evaluate the analyte concentration-signal strength relationship and are used to determine the analyte by means of a suitable method (correlation).

The at least two zones in the method according to the present invention in or on the test element are referred to in the following as analyte detection zone (abbreviation: detection zone) and control zone for better clarity and distinguishability. These terms can also be retained when according to conventional linguistic usage they are unusual, for example when binding partners having different affinity are accommodated in the zones and therefore the signal can only be observed when a threshold analyte concentration is exceeded.

The present invention also encompasses methods in which more than one detection zone and/or more than one control zone are evaluated on a test element. For example, the method can also be used to evaluate test elements which contain a detection line comprising high affinity binding partners, a detection line comprising low affinity binding partners and a control zone (for example containing immobilized analyte analogue).

The present invention in accordance with another embodiment is further directed to the extension of the measuring range of immunological test devices by means of the additional quantitative evaluation of the control line in sandwich assays. This line is usually only used as a function control for the user and is not used to quantify the analyte. However, as the analyte content increases, more and more antibody-labelled conjugate is captured on the signal line or saturated with analyte so that less and less antibody-label conjugate (e.g., antibody-gold conjugate) is bound on the control line. Hence the signal strength of the control line decreases with increasing analyte concentration. The dynamic measuring range and the slope of the calibration curve (and thus also the precision at higher concentrations) can be considerably improved by simultaneous measurements of the signal strength (for example by reflectance or fluorescence measurement) at the control line and at the signal line and by offsetting the two signal intensities using a suitable algorithm.

This of course applies analogously to test elements that are based on specific binding reactions other than immunological binding reactions. Correspondingly specific binding reactions are known to a person skilled in the art. The following binding pairs are mentioned as examples:

A) antibody with hapten, antigen or other antibodies (for example species-specific antibody-antibody interactions) where in some cases fragments of these species are also sufficient;
B) biotin with avidin or streptavidin;
C) hormone with hormone receptor;
D) sugar with lectin;
E) nucleic acid with complementary nucleic acid and such like.

For better understandability and clarity immunological binding pairs are considered in more detail in the following, i.e., the binding pairs antibody with hapten or antigen or antibody without, however, implying a limitation to this preferred but nevertheless not only embodiment of the invention.

The method according to an embodiment of the invention is used in particular to determine the concentration of an analyte in the sample with the aid of an immunological test element. In this connection the test element has an analyte detection zone as well as a control zone. The sample is brought into contact with the test element and with the specific reagents for the analyte and the analyte, if it is present in the sample, results in a detectable signal in the analyte detection zone by interaction with the specific reagents. The measured signal depends on the amount of analyte in the sample. A portion of the specific reagents that has not interacted with the analyte or the reagents in the detection zone results in a detectable signal in the control zone. It is important in this connection that this signal that is detected in the control zone also depends on the amount of analyte in the sample. The signals in the analyte detection zone and in the control zone are measured and related to one another, for example offset against one another. The result of the offsetting is compared with a calibration curve and finally the analyte concentration is determined.

Analytes that are suitable according to the invention are analytes that can be detected on the basis of a specific binding pair relationship. In the typical case of an immunological detection these can be antibodies, antigens, haptens (in this case including fragments thereof). The following immunological detectable analytes are typical: human chorionic gonadotropin ("hCG"), brain natriuretic peptide ("BNP"), N-terminal prohormone brain natriuretic peptide ("(NT-)proBNP"), troponin I, troponin T, myoglobin, D-dimer, C-reactive protein ("CRP"), human immunodeficiency virus ("HIV"), hepatitis C virus ("HCV"), CD40, creatine kinase-MB isoenzyme ("CK-MB"), thyroid stimulating hormone ("TSH"), etc.

According to the invention all liquid sample materials or sample materials that can be converted into a liquid form are suitable as a sample from which the analyte can be determined. In particular, body fluids such as blood and fractions derived therefrom (serum, plasma), saliva, urine, cerebrospinal fluid, sperm, interstitial fluid, sweat and such like are suitable. Also suitable are sample materials that are not liquid but can be transferred into a liquid phase by dissolution or suspension in solvents and in particular in aqueous solvents.

The immunological test elements that can be used according to certain embodiments of the present invention are well-known to a person skilled in the art. Analyte detection with the aid of such test elements is based on a specific interaction between the analyte and a binding partner. Such interactions include the binding pairs antigen/antibody, antibody/antibody, hapten/antibody, antigen fragment/antibody, antibody fragment/antibody, etc. As already mentioned above the test elements usually contain a material through which a flow is possible (e.g., paper, fleece, membrane, capillary channel) said material being optionally attached to an inert support. Each test element typically has one or more sample application zones, suction zones, chromatography zones, detection zones, reaction zones and control zones. It is only important for the invention that at least one (analyte) detection zone and at least one control zone are present.

A spatially very restricted area in or on the material through which a flow is possible that is separated from the control zone serves as an analyte detection zone in which a species that is a measure for the analyte is bound during the course of the intended use of the test element in such a manner that it can be detected visually, optically or in another manner. Typically a detectable binding partner for the analyte, for example an appropriately labelled anti-analyte antibody, is bound in the analyte detection zone by means of a specific interaction. For this purpose a corresponding immobilized binding partner is located in the analyte detection zone such as an antibody against the analyte (so that a detectable sandwich complex consisting of an immobilized antibody, analyte and detectably labelled antibody can form) or a species of another binding partner such as an immobilized (poly) (strept)avidin (so that a previously formed sandwich complex consisting of biotinylated antibody, analyte and detectably labelled antibody can form). The structure, function and further modifications of such detection zones are well-known to a person skilled in the art.

A spatially very restricted area that is separate from the analyte detection zone and is usually located downstream thereof on or in the material through which a flow is possible is typically used as a control zone in which the species is bound in the course of the intended use of the test element independently of the presence of the analyte in the sample in such a manner that it can be detected visually, optically or in another manner. The control zone is usually used as a function control of the test element. A signal in the control zone verifies that the sample has correctly flowed through the flow-through support and ideally that the corresponding binding reagents are functional. Typically a detectable binding partner for the analyte, for example an appropriately labelled anti-analyte antibody, is bound in the control zone by means of a specific interaction. For this purpose a corresponding immobilized binding partner such as an antibody against the labelled anti-analyte antibody is present in the control zone (so that a detectable complex consisting of immobilized antibody and detectably labelled antibody can form) or an immobilized analyte analogue is present in the control zone (so that a complex consisting of an analyte and detectably labelled antibody can form). The structure, function and further modifications of such control zones are well-known to a person skilled in the art.

The specific reagents (also referred to synonymously as "specific binding partners") that are contained in the test element or are to be added to the test element or to the sample undergo a selective (binding) reaction with the analyte or the immobilized binding partners on the support. They allow direct or indirect conclusions to be drawn about the amount of analyte present in the sample.

Typical binding partners are antibodies ("AB"), in particular polyclonal antibodies ("PAB") or monoclonal antibodies ("MAB") as well as antigens and haptens and fragments thereof, provided they are active for the purposes of the specific analyte detection.

Typically a portion of the binding partners is provided on the test device in such a manner that they can be detached from the test device by the sample liquid for example by impregnating suitable support materials such as fleeces, membranes, etc., or by applying and drying them in corresponding (capillary) channel structures.

However, it is also possible to add at least one of the binding partners in the form of dissolved reagents to the rapid test, for example to add the reagent solution to the sample or to apply the reagent solution to the test device independently of the sample. According to the present invention it is also possible to use all specific binding partners in one solution or in several solutions for the rapid test. In this case only one additional binding partner is in the detection zone on the test device which can capture the correspondingly labelled specific binding partner and thus indirectly bind the analyte to a solid phase of the rapid test. Analogously there is a binding partner in the control zone which can capture the correspondingly labelled specific binding partner without requiring a direct involvement of the analyte.

One of the binding partners immobilized in the detection zone as well as in the control zone leads in principle to a detectable signal in these zones. In this connection it is possible for the signals in the two zones to be based on different principles. More typically, the signal in the analyte detection zone as well as in the control zone are based on the same principles. Detectable signals are for example optically or visually detectable changes in color, luminescence and in particular fluorescence signals, radioactive radiation and such like. The detectable signal is generated by an appropriately labelled species (binding partner) which, as described above, is bound in the analyte detection zone or in the control zone. The following come inter alia into consideration according to the present invention as a label of the binding partner: particulate labels such as the use of colored latices, polymer labels or semiconductor nanocrystals (so-called quantum dots) or metal (sol) labels (gold, selenium, etc.) as well as non-particulate labels (enzyme, radioisotope, fluorescent labels) and such like.

Depending on the label used other detection methods are of course necessary and possible (e.g., fluorescence measurement, radioactivity measurement, determination of enzyme activity, etc.). These detection methods allow the measurement of the signals generated in the analyte detection zone and control zone especially with the aid of appropriately constructed measuring instruments. These are known to a person skilled in the art. However, according to the present invention, the signal in the analyte detection zone as well as that in the control zone is detected by the measuring instrument. Suitable measuring instruments and methods for evaluating test elements are known to a person skilled in the art. The "Cardiac Reader" system from Roche Diagnostics GmbH, Mannheim is mentioned as a typical example of a measuring instrument. In this case an immunological test strip is illuminated by means of one or more light sources (e.g., LEDs) and the grey values of the detection zone (signal line) and of the control zone are determined by means of spatially resolved reflectance measurement. A corresponding measuring and evaluation method is known for example from U.S. Pat. No. 5,717,778.

According to the invention the signals from the control zone as well as from the detection zone are detected and offset against one another by suitable mathematical methods. This for example takes place in a central computing unit of the measuring instrument. According to the present invention, both signals are dependent on the analyte concentration at least within certain concentration ranges of the analyte. The dynamic measuring range of the test elements can thus be extended (compared to only evaluating the signal in the detection zone) by means of suitable mathematical methods that are elucidated in more detail in connection with the following examples.

The analyte concentration is determined as usual from the measured signals of the detection and control zones by comparing the measured values with corresponding calibration curves obtained by measuring standard solutions containing known amounts of analyte. The signals of the detection line as well as of the control line are typically used to establish the calibration curve.

A possible implementation of the method according to an embodiment of the present invention provides that the reagents that lead to a detectable signal in the analyte detection zone and in the control zone have a different affinity for or reactivity with the analyte. Lower affinity or less reactive antibodies against the analyte are preferably involved in the signal generation in the control zone than in the analyte detection zone.

An alternative possible implementation of the method according to the invention provides that the reagents that lead to a detectable signal in the analyte detection zone and in the control zone generate detectable signals of different strengths due to different principles of interaction with the analyte or with other reagents involved in the analyte detection. In particular, antibodies directed against the analyte can be bound in the analyte detection zone and analyte or analyte analogue can be bound in the control zone. It is also possible that the binding partner immobilized in the control zone binds to another epitope of the antibody or to a heterologous structural element that was added synthetically to the antibody or that a species-specific antibody against the antibody to be immobilized is immobilized in the control zone. All these variants are known to a person skilled in the art.

One possibility of extending the measuring range up to very high concentrations results when a so-called high dose Hook effect is present. In this case the signal line intensity decreases again at very high analyte concentrations since the offered amount of antibody is no longer sufficient to form a sandwich complex in every case. There is an increasing formation of complexes consisting of analyte and in each case one antibody (conjugate). In this concentration range the intensity or the concentration dependency of the control line may be too weak to be evaluated. In contrast the decrease in intensity of the signal line can be evaluated as a function of the concentration. Hence, for this case there are three evaluation ranges:

1. Increase in the intensity of the signal line as a function of the concentration.
2. Decrease in the intensity of the control line as a function of the concentration.
3. Decrease in the intensity of the signal line as a function of the concentration.

An automatic differentiation between the three said ranges can for example be achieved by the following algorithm:
A) If the reflectance at the signal line is larger than X1% and the reflectance at the control line is less than Y1%, only evaluate the signal line and use the calibration curve for analyte concentrations from A1 to A2 mg/ml.
B) If the reflectance at the signal line is less than X2% and the reflectance at the control line is larger than Y2% and less than Y3%, only evaluate the control line and use the calibration curve for analyte concentrations from A3 to A4 mg/ml.

C) If the reflectance at the signal line is larger than X3% and the reflectance at the control line is larger than Y4%, only evaluate the signal line and use the calibration curve for analyte concentrations from A5 to A6 mg/ml.

The invention is elucidated in more detail on the basis of the following examples and figures, which are intended to illustrate the invention, but not limit the scope thereof. Although only immunological test devices are shown exemplarily in the examples which use gold-labelled binding partners and are measured by reflectance photometry, the invention is not limited hereto. In addition to immunological interactions that are based on antigen (or hapten)-antibody binding pairs, other binding pairs are also possible and in particular hormone-receptor, sugar-lectin, nucleic acid-complementary nucleic acid, biotin-(strept)avidin and such like. Apart from gold labels, other particulate labels are also possible such as for example the use of colored latices, polymer labels or semiconductor nanocrystals (so-called quantum dots) or other metal (sol) labels as well as non-particulate labels (enzyme, radioisotope, fluorescent labels) and such like. Depending on the label used other detection methods are of course also required and are possible (e.g., fluorescence measurement, radioactivity measurement, determination of enzyme activity, etc.). A person skilled in the art knows these variations in a large number of embodiments.

EXAMPLES

Figure 1:
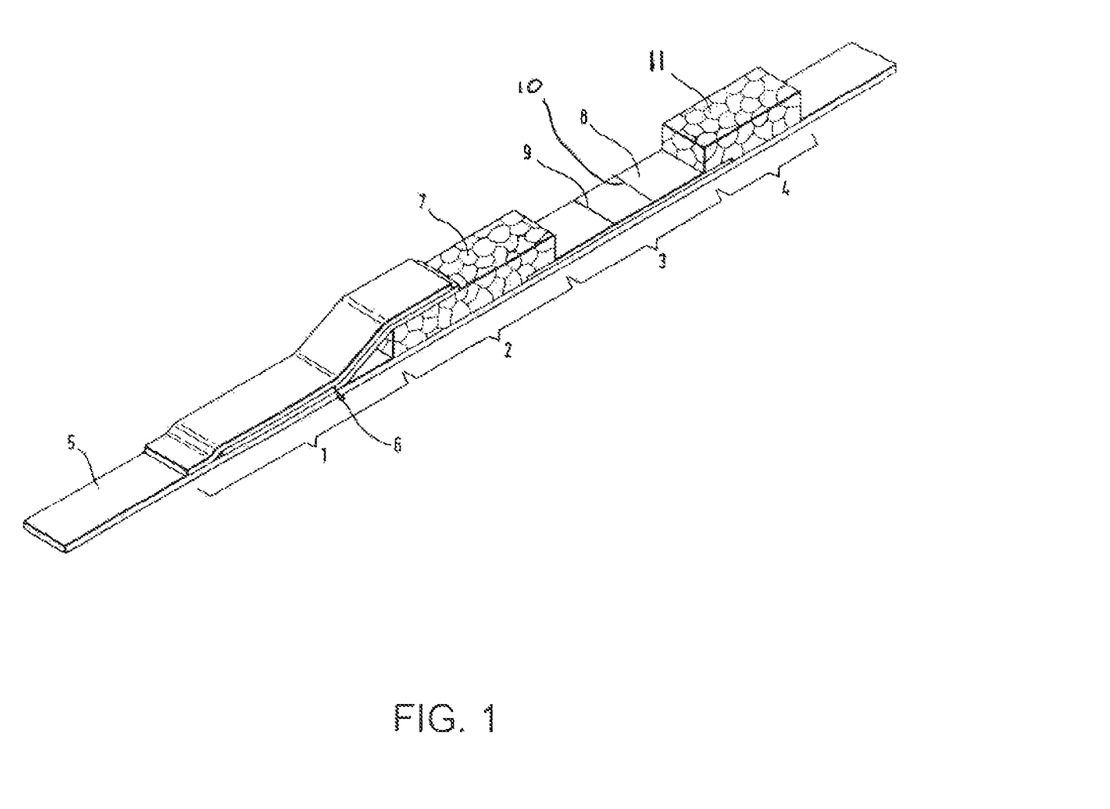
FIG. 1 shows schematically an embodiment of a test device that can be used according to the invention in the form of an immunochromatographic test strip.

1) Preparation of a Test Device to Determine Antigens from Whole Blood (cf FIG. 1)

The test device (FIG. 1) consists of a support material (5) on which a sample application zone (1), an erythrocyte separation zone (2), a detection zone (3) and a suction zone (4) is applied. A sample application matrix (6) which partially overlaps the erythrocyte separation matrix (7) is disposed in the sample application zone (1). The erythrocyte separation matrix (7) in turn overlaps somewhat the detection matrix (8) (detection zone) on which polystreptavidin is immobilized in the form of a line (9) as a detection line and antigen or antigen analogue is immobilized for example as a synthetic or recombinant antigen peptide in the form of a line (10) as a control line. A suction matrix (11) overlaps somewhat the detection matrix (8). All those reagents are accommodated in the sample application matrix (6) which are required to form a complex with the analyte to be detected. In the present case the sample application zone consists of two fleeces lying on top of one another where the first (gold fleece) is impregnated with a gold-labelled antibody against the analyte and the second fleece (biotin fleece) contains a biotinylated antibody against the analyte. In this case the analyte is an antigen that occurs in blood, in particular troponin T, NT-proBNP or D-dimer.

A polyester foil (Putz) having a thickness of 350 µm is used as the support layer 5. A polyester fleece (Roche Diagnostics) having a thickness of 360 µm is used as the sample application matrix 6. A glass fibre fleece (Roche Diagnostics) of 1.8 mm in thickness is used as the erythrocyte separation matrix 7. A nitrocellulose membrane (Sartorius) having a thickness of 140 µm is used as the detection matrix 8. A glass fibre fleece (Roche Diagnostics) of 1.8 mm in thickness is used as the suction matrix 11. The individual components (6, 7, 8, 11) are glued slightly overlapping onto the support layer 5 by means of hot-melt adhesive as shown in FIG. 1.

Figure 2:
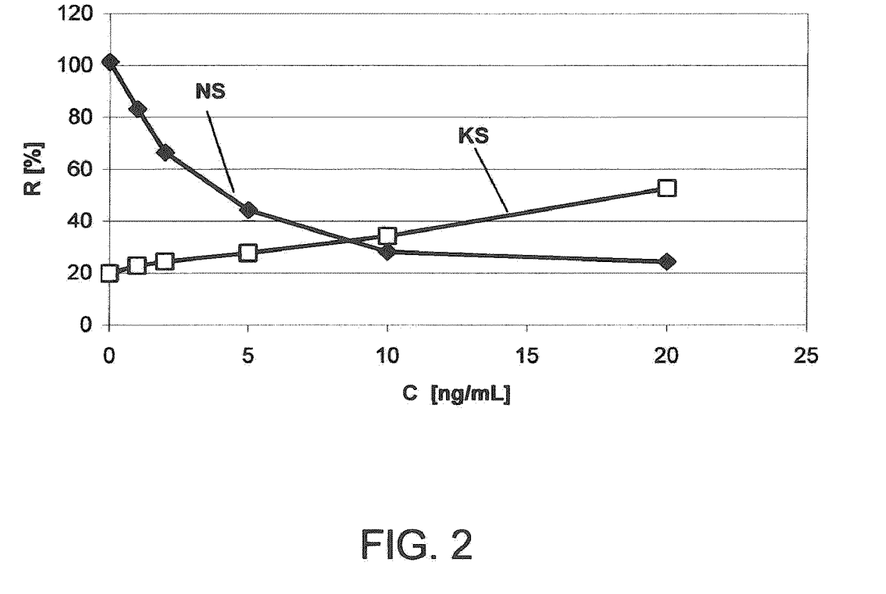
FIG. 2 shows relative reflectance values (R in %) for the evaluation of the detection line (NS) and the control line (KS) as a function of the troponin T concentration in the sample (C in ng/ml)
Figure 3:
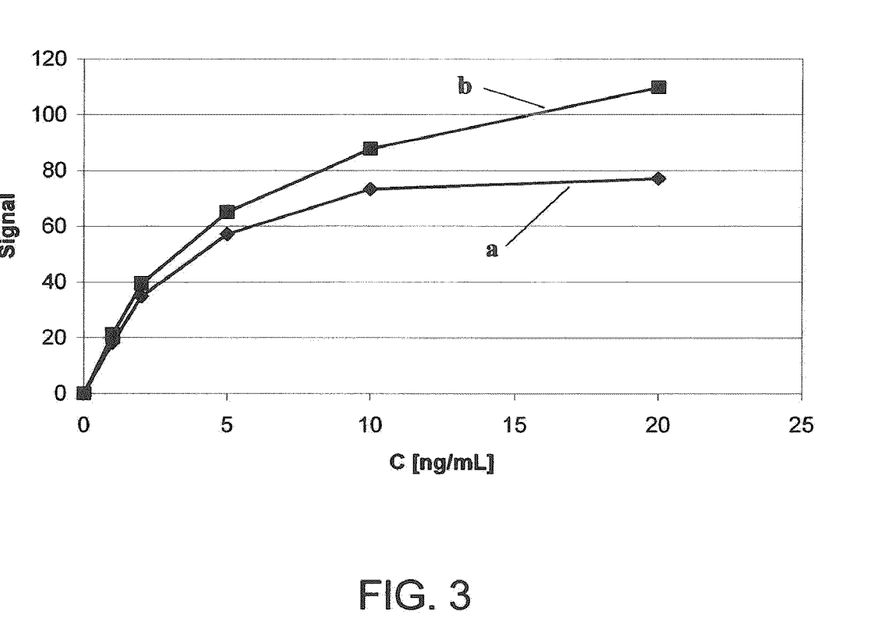
FIG. 3 shows the calibration curves for a troponin T test strip which result from using the algorithms a) (prior art) and b) (invention) on the measured values from FIG. 2 as elucidated in more detail in example 2.
Figure 4:
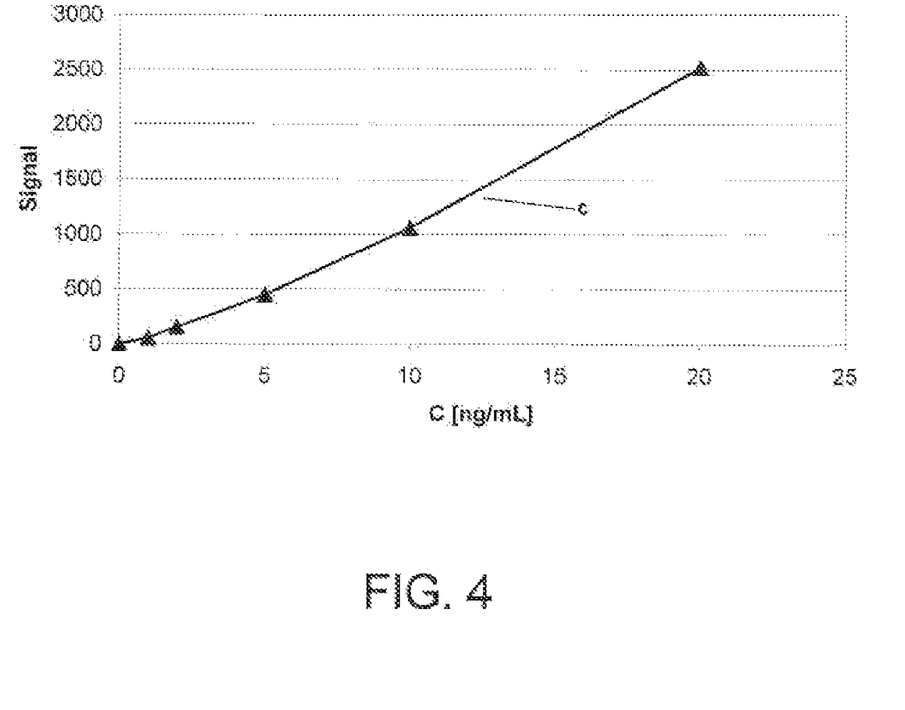
FIG. 4 shows the calibration curve for a troponin T test strip which is derived by using the algorithm c) (invention) which is elucidated in more detail in example 2 on the measured values from FIG. 2.

The impregnation formulations for the gold and biotin fleeces of the examples shown are:

proBNP Test Strip:
   biotin fleece: 100 mM Hepes pH 7.4, 0.1% Tween®, biotinylated antibody against the analyte
   gold fleece: 100 mM Hepes pH 7.4, antibody against the analyte as gold conjugate Troponin T Test Strip:
   biotin fleece: 100 mM MES pH 5.6, biotinylated antibody against the analyte
   gold fleece: 100 mM succinic acid pH 5.6, 0.1% Tween®antibody against the analyte as gold conjugate D-Dimer Test Strip:
   biotin fleece: 100 mM Hepes pH 7.4, 0.1% Tween®, biotinylated antibody against the analyte
   gold fleece: 100 mM Hepes pH 7.4, antibody against the analyte as gold conjugate 2) Evaluation of a Test Strip for the Troponin T Determination (FIGS. 2 to 4)

Whole blood samples to which recombinantly produced troponin T had been added in different amounts were applied to troponin T test strips according to example 1. The strips were evaluated by two methods according to the invention (variants b) and c) see below) as well as by the conventional method (variant a) for comparative purposes. The reflectance was determined for the detection line (NS) (9) and the control line (KS) (10) using a conventional measuring instrument based on a CCD camera (Cardiac Reader, Roche Diagnostics GmbH) and the signals were computed according to the following algorithm:

a) |Ref NS(0)−Ref NS(c)|
   b) |Ref KS(0)−Ref KS(c)|+|Ref NS(0)−Ref NS(c)|
   c) |Ref KS(0)−Ref NS(c)|*|Ref NS(0)−Ref NS(c)| where the algorithm alternative a) only represents the conventional evaluation of the detection line according to the prior art. According to the invention the detection line signal as well as the control line signal are both used in b) and c) for the evaluation.

The abbreviations in the formulae have the following meanings:
   Ref NS (0) reflectance of the detection line in % at an analyte concentration 0
   Ref NS (c) reflectance of the detection line in % at an analyte concentration c
   Ref KS (0) reflectance of the control line in % at an analyte concentration 0
   Ref KS (c) reflectance of the control line in % at an analyte concentration c In FIG. 2 the relative reflectance values (R in %) for the evaluation of the detection line (NS) and of the control line (KS) are shown as a function of the troponin T concentration in the sample (c in ng/ml). FIG. 2 illustrates the decrease in signal (increase in reflectance) of the control line as the analyte concentration increases with a simultaneous increase in the signal (decrease in the reflectance) of the detection line.

FIG. 3 shows the calibration curves for a troponin T test strip which are derived by using the algorithms elucidated above a) (prior art) and b) (invention) on the measured values from FIG. 2. The calibration curve for a troponin T test strip is shown in FIG. 4 which is obtained by using the algorithm c) (invention) that is elucidated above on the measured values from FIG. 2. Whereas concentrations could only be determined up to about 10 ng/ml with this test when only the detection line is evaluated (algorithm a)), concentrations of more than 20 ng/ml can still be determined by evaluating the KS and NS according to algorithms b) and c).

Figure 5:
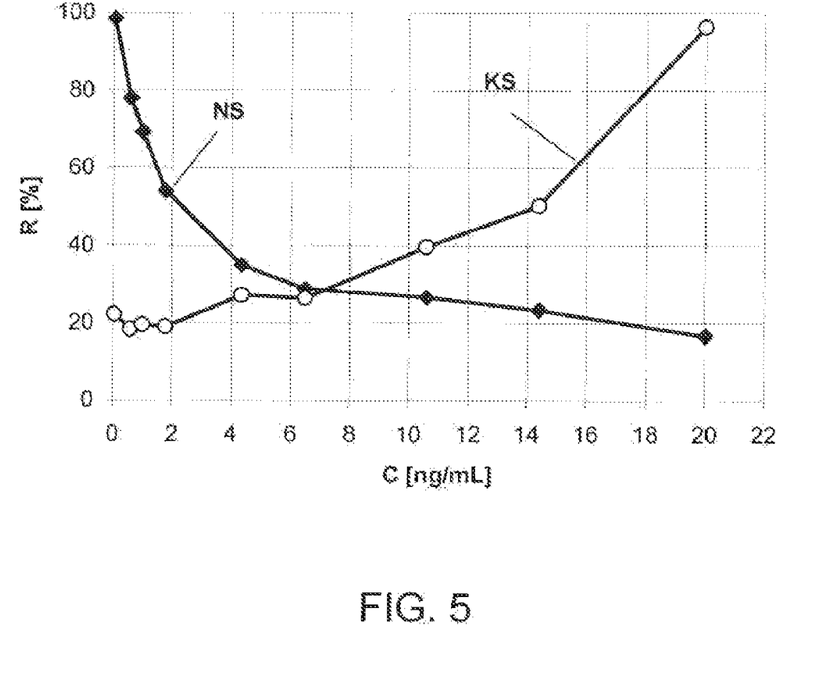
FIG. 5 shows the relative reflectance values (R in %) for the evaluation of the detection line (NS) and the control line (KS) as a function of the NT-proBNP concentration in the sample (C in ng/ml)
Figure 6:
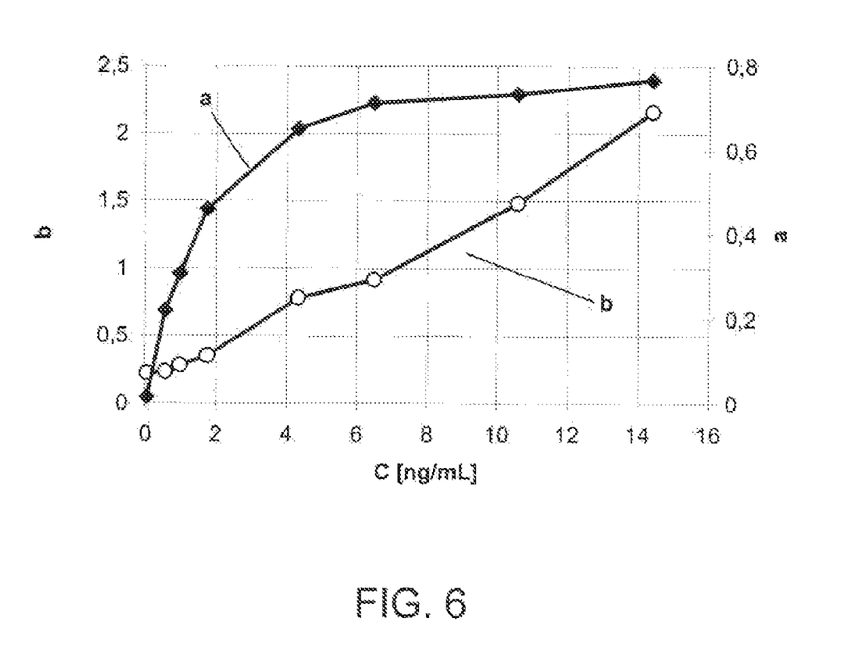
FIG. 6 shows the calibration curves for an NT-proBNP test strip which are derived by using the algorithms a) (prior art) and b) (invention) that are elucidated in more detail in example 3 on the measured values from FIG. 5.

3) Evaluation of a Test Strip for the NT-proBNP Determination (FIGS. 5 to 6)

Whole blood samples to which synthetic NT-proBNP had been added in different amounts were applied to NT-proBNP test strips according to example 1. The strips were evaluated by the method according to the invention (variant b) see below) as well as by the conventional method (variant a)) for comparative purposes. The reflectance was determined for the detection line (NS) (9) and for the control line (KS) (10) using a conventional measuring instrument based on a CCD camera (Cardiac Reader, Roche Diagnostics GmbH) and the signals were computed according to the following algorithm:
- a) 1−Ref NS(c)
- b) Ref KS(c):Ref NS(c)

where the algorithm alternative a) only represents the conventional evaluation of the detection line according to the prior art. According to the invention the detection line signal as well as the control line signal are both used in b) for the evaluation.

The abbreviations in the formulae have the same meaning as in example 2.

In FIG. 5 the relative reflectance values (R in %) for the evaluation of the detection line (NS) and of the control line (KS) are shown as a function of the NT-proBNP concentration in the sample (c in ng/ml). FIG. 5 illustrates the decrease in signal (increase in reflectance) of the control line as the analyte concentration increases with a simultaneous increase in the signal (decrease in the reflectance) of the detection line.

FIG. 6 shows the calibration curves for a NT-proBNP test strip which are derived by using the algorithms elucidated above a) (prior art) and b) (invention) on the measured values from FIG. 5. Whereas concentrations could only be determined up to about 6 ng/ml this test when only the detection line is evaluated (algorithm a)), concentrations of more than 14 ng/ml can still be determined by evaluating the KS and NS according to algorithm b).

Figure 7:
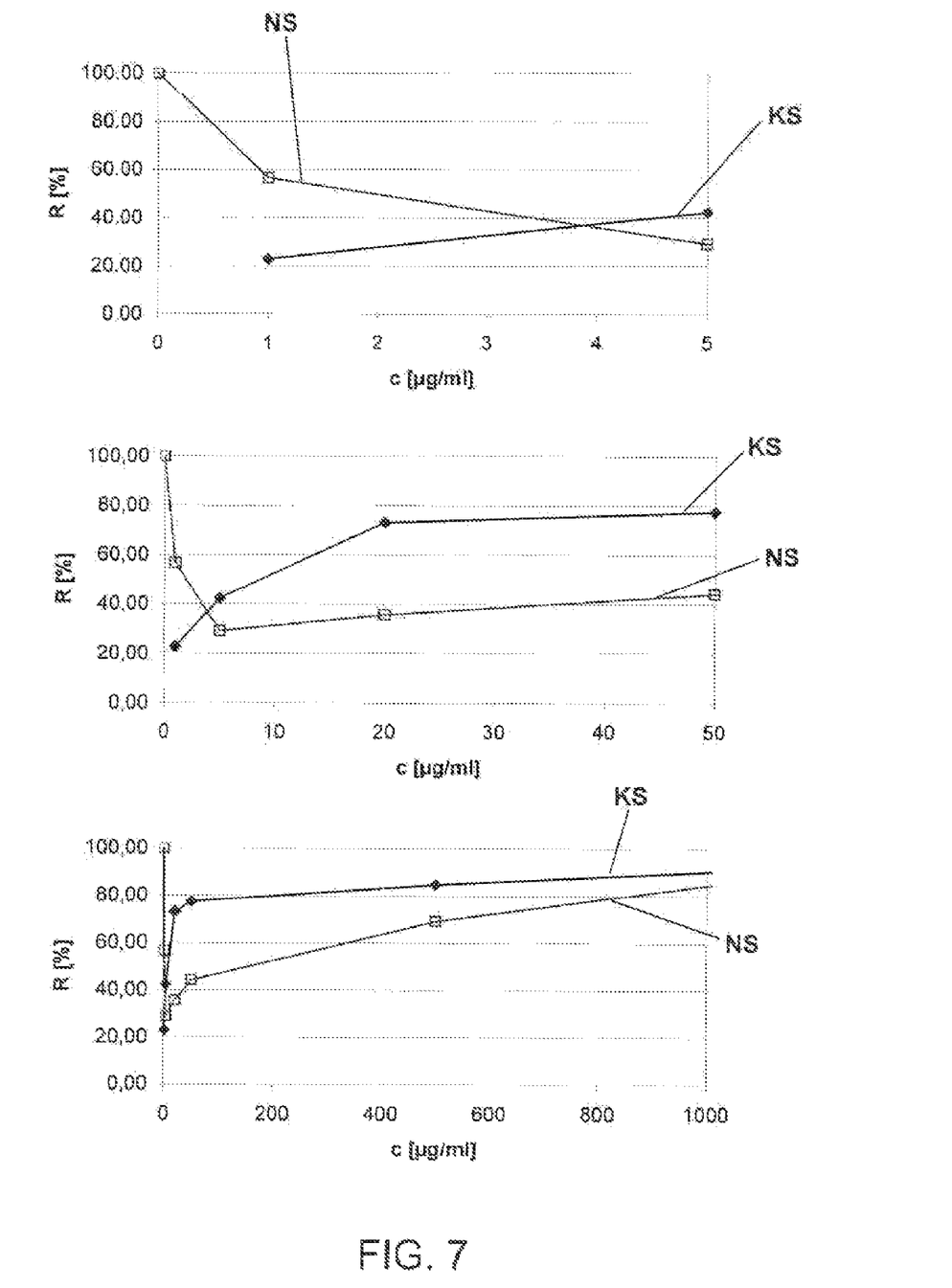
FIG. 7 shows the relative reflectance values (R in %) for the evaluation of the detection line (NS) and the control line (KS) as a function of the D-dimer concentration in the sample (c in μg/ml) in three subfigures (which each cover different concentration ranges).

4) Evaluation of a Test Strip for the D-Dimer Determination (FIG. 7)

Whole blood samples to which fibrin fragments containing D-dimer were added in different amounts were applied to D-dimer test strips according to example 1 (biotinylated antibody which is directed against the analyte is immobilized on the detection line; in contrast the control line consists of immobilized fibrin fragments which contain the D-dimer structural element; free gold conjugate antibodies can be bound to these). The strips were evaluated by the method according to the invention (variant b, see below) as well as by the conventional method (variant a) for comparative purposes. The reflectance was determined for the detection line (NS) (9) and the control line (KS) (10) using a conventional measuring instrument based on a CCD camera (Cardiac Reader, Roche Diagnostics GmbH) and the signals were computed according to the following algorithm:
- a) Ref NS (c)
- b) 1.) If the reflectance at the signal line is larger than 30% and the reflectance at the control line is less than 40%, only evaluate the signal line (Ref NS (c)) and use the calibration curve for analyte concentrations of 0 to 3 µg/ml.
  - 2.) If the reflectance at the signal line is less than 50% and the reflectance at the control line is larger than 40% and less than 70%, only evaluate the control line (Ref KC (c)) and use the calibration curve for analyte concentrations of 3 to 20 µg/ml.
  - 3.) If the reflectance at the signal line is larger than 30% and the reflectance at the control line is larger than 70%, only evaluate the signal line (Ref NS (c)) and use the calibration curve for analyte concentrations of 20 µg/ml to 1000 µg/ml.

where the algorithm alternative a) only represents the conventional evaluation of the detection line according to the prior art. According to the invention the detection line signal as well as the control line signal are used in b) for the evaluation.

The abbreviations in the formulae have the same meaning as in example 2.

The relative reflectance values (R in %) for the evaluation of the detection line (NS) and the control line is shown in FIG. 7 as a function of the D-dimer concentration in the sample (c in µg/ml).

The evaluation can be carried out as usual by means of the reflectance decrease (intensity increase) of the signal line up to a D-dimer concentration of ca. 3 µg/ml. The reflectance increase (intensity decrease) of the control line can be evaluated up to ca. 20 µg/ml. At an analyte concentration of above 20 µg/ml the concentration dependency of the control line signal is too low. Above about 20 µg/ml up to >1000 µg/ml the reflectance increase (intensity decrease) of the signal line can be used for the evaluation. Since the lower limit of the measuring range is <0.5 µg/ml, a dynamic factor of >1000 is achievable.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

I claim:

1. A method for determining the concentration of an analyte in a sample comprising:
   a) providing a test element comprising at least one first zone and at least one second zone;
   b) contacting the sample with the test element and at least one detectable binding partner capable of specific binding reaction with the analyte;
   c) forming a complex comprising at least said detectable binding partner, said analyte, and an immobilized binding partner comprising an analyte specific antibody localized in said first zone;
   d) forming a complex comprising at least said detectable binding partner said analyte, and an immobilized binding partner comprising an analyte specific antibody localized in said second zone;

e) measuring a first detectable signal (NS) in the first zone, wherein said first signal is dependent on the amount of said analyte in said sample;
f) measuring a second detectable signal (KS) in the second zone, wherein said second signal is also dependent on the amount of analyte in the sample;
g) offsetting said first and said second signals using one of the following algorithms:

[KS(0)-KS(c)] + [(NS(0)-NS(c)],
[KS(0)-NS(c)] * [NS(0)-NS(c)], and
KS(c):NS(c), wherein,
NS(0)=signal in the first zone at an analyte concentration 0;
NS(c)=signal in the first zone at an analyte concentration c;
KS(0)=signal in the second zone at an analyte concentration 0; and
KS(c)=signal in the second zone at an analyte concentration c, h) comparing the offset of said first and said second signals with a calibration curve; and
i) determining the presence or amount of the analyte, wherein the immobilized binding partner localized in said first zone and the immobilized binding partner localized in said second zone have different affinities for or reactivities to the analyte.

2. The method according to claim 1, wherein said first and said second signals are used to establish the calibration curve.

3. The method according to claim 1, wherein the detectable binding partner generates detectable signals of different strengths due to different principles of interaction with the analyte or with other reagents involved in the analyte detection.

4. The method according to claim 1, wherein said first zone is a detection zone and said second zone is a control zone.

5. The method according to claim 4, wherein said first zone comprises a first detection line comprising immobilized high affinity binding partners and said second zone comprises a second detection line comprising immobilized low affinity binding partners.

6. The method according to claim 1, wherein said first and said second signals are visually or optically detectable.

7. The method according to claim 1, wherein said test element is an immunological test element.

8. The method according to claim 1, wherein said specific binding reaction is an immunological binding reaction.

9. The method according to claim 1, wherein said analyte is selected from antibodies, antigens, haptens, and fragments thereof.

10. The method according to claim 1, wherein said analyte is selected from human chorionic gonadotropin, brain natriuretic peptide, N-terminal prohormone brain natriuretic peptide, troponin I, troponin T, myoglobin, D-dimer, C-reactive protein, human immunodeficiency virus, hepatitis C virus, CD40, creatine kinase-MB isoenzyme, thyroid-stimulating hormone, and combinations thereof.

11. The method according to claim 1, wherein said sample is a liquid.

12. The method according to claim 1, wherein said sample is a body fluid selected from whole blood, blood fractions, saliva, urine, cerebrospinal fluid, sperm, intestinal fluid, sweat, and combinations thereof.

13. The method according to claim 1, wherein said sample is blood serum or blood plasma.

14. The method according to claim 1, wherein said sample is capable of being transferred into a liquid phase by dissolution or suspension in solvents.

15. The method according to claim 14, wherein said sample is dissolved or suspended in an aqueous solvent.

* * * * *